United States Patent [19]

Badwal et al.

[11] Patent Number: 4,789,454

[45] Date of Patent: Dec. 6, 1988

[54] LOW TEMPERATURE SOLID ELECTROLYTE OXYGEN SENSOR

[75] Inventors: Sukhvinder P. S. Badwal, Mulgrave; Michael J. Bannister, Glen Waverley, both of Australia

[73] Assignee: Commonwealth Scientific and Industrial Research Organization, Australia

[21] Appl. No.: 15,199

[22] Filed: Feb. 17, 1987

Related U.S. Application Data

[63] Continuation of Ser. No. 666,960, Oct. 2, 1984, abandoned.

[30] Foreign Application Priority Data

Feb. 2, 1983 [AU] Australia .............................. PF7857

[51] Int. Cl.⁴ .......................................... G01N 27/58
[52] U.S. Cl. .................................... 204/424; 204/421; 204/422
[58] Field of Search ................ 204/1.5, 421, 422, 423, 204/424, 425, 426, 427, 428, 429; 427/126.2, 126.3, 126.5

[56] References Cited

U.S. PATENT DOCUMENTS

| Re. 28,792 | 4/1976 | Ruka et al. | 204/425 X |
| 3,342,558 | 9/1967 | Reinecke | 204/424 X |
| 3,619,381 | 11/1971 | Fitterer | 204/423 X |
| 3,791,954 | 2/1974 | Noda et al. | 204/423 |
| 4,158,166 | 6/1979 | Isenberg | 204/426 X |
| 4,193,857 | 3/1980 | Bannister et al. | 204/428 |

OTHER PUBLICATIONS

Pound et al., "The Electrolysis . . . Electrodes", Int. J. Hydrogen Energy, vol. 6, No. 5, pp. 473–486, 1981.
Badwal et al., "Unania–ytria . . . Application", J. of Material Science, 14 (1979), pp. 2353–2365.
M. J. Bannister, "The Standard . . . Temperature", J. Chem. Thermodynamics, 1984, 16, 787–792.
Badwal et al., "Low . . . Sensor", printed from Ad. in Ceramics, vol. 12, Sc. and Techn. of Zirconia, II, Copyright 1984 by American Ceramic Soc.

Primary Examiner—John F. Niebling
Assistant Examiner—Nam X. Nguyen
Attorney, Agent, or Firm—Sughrue, Mion, Zinn, Macpeak, and Seas

[57] ABSTRACT

An electrode for a solid electrolyte oxygen sensor, characterized in that the electrode comprises a surface layer on the solid electrolyte, said surface layer consisting of or containing a solid solution in urania of one or more other metal oxides with oxygen/metal atom ratio equal to or less than two, provided that at least one of said other metal oxides has an oxygen/metal atom ratio less than two.

5 Claims, 6 Drawing Sheets

LOW TEMPERATURE SOLID ELECTROLYTE OXYGEN SENSOR

This is a continuation of application Ser. No. 666,960, filed 10-2-84, now abandoned.

This invention concerns electrode materials for solid electrolyte sensors which are used to measure the oxygen potential of gases or molten metals. The electrode materials of this invention enable such oxygen sensors to operate accurately at temperatures down to 300° C.

Measurement of the oxygen potential of gases and molten metals using solid electrolyte sensors is well documented. For example, a sensor designed primarily for determinations in molten copper is described in Australian Pat. No. 466,251 and in the corresponding patents, U.S. Pat. No. 4,046,661, United Kingdom No. 1,347,937, Canadian No. 952,983, Belgian No. 782,180, Japanese No. 80 17340 and West German Offenlegungsschrift No. 22 18227.0. Modifications, particularly to the electrolyte, to improve the sensor for measurements in gases are described in Australian Pat. No. 513,552 and its equivalents U.S. Pat. No. 4,193,857, United Kingdom No. 1,575,766, Canadian No. 1,112,438, West German Offenlegungsschrift document No. 27 54522.8 and Japanese patent application No. 146208/77.

The solid electrolyte oxygen sensor uses the fact that when a solid membrane of a material with good oxygen ion conductivity and negligible electronic conductivity, termed a solid electrolyte, is held with its opposite faces in contact with materials having different oxygen potentials, an emf is established across the membrane. If one of the oxygen-containing materials is the gas or molten metal under investigation and the other is a reference material of known oxygen potential, then the emf (E) is given by the Nernst relationship:

$$E = \frac{RT}{nF} \cdot \ln\left(\frac{P_{O_2} \text{ (reference material)}}{P_{O_2} \text{ (test material)}}\right) \quad (1)$$

where:
R = the gas constant,
T = the absolute temperature,
n = 4 (the number of electrons transferred per oxygen molecule),
F = the Faraday constant, and
$P_{O_2}$ = the oxygen partial pressure.

This emf is measured using electrodes, reversible to the $O_2/O^{2-}$ redox equilibrium, placed in electrical contact with the opposing faces of the solid electrolyte membrane.

Australian Pat. No. 466,251 describes various geometrically distinct forms of solid electrolyte oxygen sensor. The most commonly-used form is that of a tube, either open-ended or closed at one end, made entirely from the solid electrolyte. Other designs use the solid electrolyte as a disc or pellet, sealed in one end of a metal or ceramic supporting tube. In all cases the reference environment, which is generally air, is maintained on one side of the tube (commonly on the inside) and the test environment is exposed to the other side of the tube.

Many solid electrolyte materials are known to be suitable for use in oxygen sensors. Examples include zirconia or hafnia, both fully stabilized or partially stabilized by doping with calcia, magnesia, yttria, scandia or one of a number of rare earth oxides and thoria, also doped with calcia, yttria or a suitable rare earth oxide. Australian Pat. No. 513,552 discloses the addition of alumina to these solid electrolyte materials to produce a composite solid electrolyte which is particularly suitable for sealing into the end of an alumina tube, thereby making a rugged and leak-tight sensor useful for demanding industrial applications. Australian patent application No. 47828/78 and the corresponding patents or applications U.S. Pat. No. 4,240,891, United Kingdom application No. 79 19671, Canadian application No. 329,100, Japanese application No. 69529/79 and West German application No. 29 22947.8 disclose the use of magnesium aluminate spinel as an alternative to alumina, either for the supporting tube or as the inert diluent in the composite solid electrolyte material.

The electrodes on solid electrolyte oxygen sensors generally consist of porous coatings of noble metals such as platinum, gold, palladium or silver, or alloys of these elements. For measurements in gases using a gaseous reference an electrode is required on each surface of the solid electrolyte; for measurements in molten metals an electrode is required only on the reference side of the solid electrolyte, and then only if a gaseous reference is used. If a solid reference, e.g., a metal/metal oxide mixture, is used there is no need for a separate noble metal electrode; the solid reference mixture serves as the electrode.

The electrodes participate in the exchange reaction between gaseous oxygen molecules and oxygen ions in the solid electrolyte by donating or accepting electrons. The overall equilibrium at each electrode is represented by the equation:

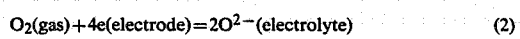

$$O_2(\text{gas}) + 4e(\text{electrode}) = 2O^{2-}(\text{electrolyte}) \quad (2)$$

The electrodes may also help to catalyse this reaction. For example platinum, the most commonly used electrode material on solid electrolyte oxygen sensors, shows a high catalytic activity for this oxygen exchange reaction at elevated temperatures.

Solid electrolyte oxygen sensors with noble metal electrodes are generaly used at temperatures above 600°–700° C. As the temperature is reduced below 600° C., the following characteristics become increasingly evident.

(a) The total impedance rapidly increases, reaching megohm levels.

(b) The response time increases from a fraction of a second to many minutes.

(c) An emf appears when none is predicted (zero error).

(d) The emf is not ideal (i.e. it does not follow the Nernst equation) even after correction for zero error.

(e) The emf may depend on the gas flow rate.

(f) the emf under fuel-rich conditions (e.g. gas mixtures with high $CO/CO_2$ ratios) is very greatly in error.

The increased impedance may be at least partly counteracted by controlling the electrolyte composition, in particular its impurity content, to maximise its ionic conductivity, and by increasing the ratio: electrode area/solid electrolyte membrane thickness of the sensor. Response time and emf accuracy at low temperatures may be enhanced by controlling the physical characteristics of the electrodes, i.e., porosity, particle size, layer thickness, etc. In general this means ensuring a very porous, extremely fine-grained texture in the electrodes. Noble metal electrodes, however, undergo morphology changes due to sintering and grain growth when exposed to higher temperatures, to the detriment of their subsequent low temperature performance.

One objective of the present invention is to provide electrodes for solid electrolyte oxygen sensors which enable such sensors to generate ideal (i.e. Nernstian) emfs under oxygen-excess gaseous conditions at temperatures substantially below those at which conventional noble metal electrodes begin to show non-ideal behaviour. A further objective is to provide electrodes which retain their good low temperature behaviour after exposure to temperatures as high as 900° C.

An electrode material for a solid electrolyte oxygen sensor should have the following characteristics.

(a) High electronic conductivity.

(b) High catalytic activity for the oxygen molecule-/ion exchange reaction (equation (2) above).

(c) Good thermal and mechanical match with the solid electrolyte.

(d) Structural stability under oxidising and reducing conditions.

(e) Freedom from adverse reactions with the solid electrolyte or with the external environment.

We have now found that all these criteria are satisfied by electrode materials which are solid solutions in uranium oxide of one or more other metal oxides with oxygen/metal atom ratios less than or equal to two, provided that at least one of said other metal oxides has an oxygen/metal atom ratio of less than two. The solid solutions have a face-centred cubic crystal structure similar to that of calcium fluoride (fluorite); therefore, they are isostructural with and similar in thermomechanical properties to solid electrolytes based on zirconia, hafnia or thoria. Typical oxides useful as solutes in these uranium oxide-based solid solution electrode materials are scandia ($Sc_2O_3$) and yttria ($Y_2O_3$); other oxides which dissolve in uranium oxide, such as calcia (CaO) and the rare earth oxides, are also suitable.

Solid solutions of the type herein described are known. They are listed, for example, in the compilation "Phase Diagrams for Ceramists", published by the American Ceramic Society in 1964 with supplements in 1969, 1975 and 1981. They are also described in the book "Handbook of Phase Diagrams of Silicate Systems. Vol. I. Binary Systems" by N. A. Toropov, V. P. Barzakovskii, V. V. Lapin and N. N. Kurtseva, translated from Russian by the Israel Program for Scientific Translations, published in 1972 by the U.S. Department of Commerce, National Bureau of Standards. It is known that these solid solutions have appreciable electronic conductivity because of the ease with which the uranium ion can change its valency. Many of them are known to tolerate substantial changes in oxygen/metal atom ratio without change in crystal structure and with only small changes in the size of the fluorite unit cell. S. P. S. Badwal and D. J. M. Bevan, in their article "Urania-yttria solid solution electrodes for high temperature electrochemical applications" published in the *Journal of Materials Science*, Volume 14, 1979 at page 2353, have shown that urania-yttria and urania-scandia are potentially useful as electrodes on stabilized zirconia solid electrolyte for high temperature fuel cells or for the high temperature electrolysis of steam, at temperatures in the range 800° to 1200° C. They did not suggest, nor can their results be taken to indicate, that such urania-based solid solution materials are useful as electrodes on solid electrolyte oxygen sensors, particularly at low temperatures.

German Democratic Republic patent No. 22 030 discloses high-temperature electrodes for galvanic solid electrolyte cells, in particular for fuel cells, which bear a superficial resemblance to the electrodes of the present invention. The aforesaid high temperature electrodes comprise solid electrolyte materials such as stabilized zirconia or doped thoria with the admixture of an electronically-conducting oxide such as ceria, urania, praseodymia or nickel oxide. There is no suggestion that the solid electrolyte basic ingredient is unnecessary, and urania-based solid solutions such as urania-scandia and urania-yttria are not mentioned. Furthermore, it is clear that the electrodes of German Democratic Republic Pat. No. 22 030 are intended only for high temperature use, especially in fuel cells where their current-carrying capacity is important. No suggestion is made that such electrodes are useful for low temperature oxygen sensors, which operate under potentiometric conditions with negligible current flow. Nor does the patent provide any scientific information, particularly on electrochemical behaviour, which would allow those skilled in the art to infer that the electrodes would be useful for low temperature oxygen sensors.

Belgian Pat. No. 894,044 discloses a solid electrolyte oxygen sensor whose electrodes are one or more non-stoichiometric oxides with mixed ionic and electronic conductivity. Oxides claimed to be useful as electrodes are $PrO_{2-x}$ and $TbO_{2-x}$, either singly or mixed with $CeO_{2-x}$, (where the subscript "2-x" indicates a small departure from an ideal oxygen/metal atom ratio of 2) and mixed oxides containing lanthanide group elements, transition metals and/or alkaline earth metals, specific examples being $LaCrO_3$ and $(La,Sr)CrO_3$. It is stated that these electrode materials have advantages over platinum in that they are less sensitive to trace gases such as $H_2$, CO, $SO_2$ and hydrocarbons, and to the vapours of metals such as lead. There is no suggestion that the electrode materials are intrinsically better than platinum for sensor use at low temperatures. The urania-based solid solution materials of the present invention are not mentioned in the Belgian patent, either to replace platinum for conventional sensor uses or to enable sensors to operate at low temperatures. Urania-based solid solution electrodes have not previously been used on solid electrolyte oxygen sensors, either at high or low temperatures.

Accordingly, the present invention provides an electrode for a solid electrolyte oxygen sensor, the electrode comprising a surface layer on the solid electrolyte, said surface layer consisting of or containing a solid solution in urania of one or more other metal oxides with oxygen/metal atom ratio equal to or less than two, provided that at least one of said other metal oxides has an oxygen/metal atom ratio less than two.

According to one embodiment of the invention, the surface layer consists of a thin porous coating of particles consisting of or containing the said oxide solid solution.

According to a further aspect of the invention, the surface layer consists of or contains a mixture of at least one noble metal selected from the group consisting of platinum, gold, palladium, silver and alloys of any two or more of these elements, and particles of a solid solution comprising urania and one or more other metal oxides with oxygen/metal atom ratio equal to or less than two, provided that at least one of such metal oxides has an oxygen/metal atom ratio less than two.

According to another aspect of the present invention, the surface layer comprises a thin region on and extending beneath the surface of the solid electrolyte, said region being locally enriched in a solid solution consisting of or comprising urania and one or more other metal oxides with oxygen/metal atom equal to or less than two, provided that at least one of such metal oxides has an oxygen/metal atom ratio less than two.

It is also within the scope of this invention that, in addition to the urania-based solid solution, the electrode coatings or enriched regions may contain a proportion of free uranium oxide and/or of the other oxide component or components of the solid solution.

In a preferred form of the invention the urania-based solid solution material contains one or more dopant oxides, such as $Sc_2O_3$, $Dy_2O_3$, $Y_2O_3$ or $PrO_y$ (where $y<2$), the total dopant oxide concentration falling within the range over which the fluorite solid solution is a stable phase. For example, if scandia is the solute oxide, the $Sc/(U+Sc)$ atom ratio will fall within the range 0.50 to 0.62 in air.

The invention also includes methods for producing the electrodes of the invention.

Where the surface layer is a coating, the solid solution may be applied to the solid electrolyte surface by any suitable known coating method, such as painting, sputtering or spraying. It is preferred to preform the solid solution before application although it is possible to apply the individual oxide components (or compounds which will produce them) in intimate admixture and to produce the solid solution by sintering the coating. The noble metal, if used, is applied with the solid solution (or its component oxides). Either the elemental metal or a suitable compound which can be heat-decomposed to the metal can be used.

Where the surface layer takes the form of a region at and just below the solid electrolyte surface which is locally enriched in the urania-based solid solution, such enrichment may be achieved, for example, by solid state diffusion of the oxide materials into the electrolyte surface at high temperatures; by ion implantation of the metals, followed by oxidation; or by incorporation of the oxide materials into the electrolyte surface prior to sintering.

For rapid response particularly at low temperatures, it is advantageous that such a locally-enriched surface region or coating be thin, porous and of fine particle size.

The electrode materials of this invention have permitted the construction of oxygen sensors with a low interfacial impedance between the electrode and the solid electrolyte, and whose performance under typical air-excess combustion conditions conform to the Nernst equation down to temperatures as low as 300° C. The same sensors with conventional noble metal electrodes show a much higher electrode/electrolyte interfacial impedance and depart significantly from the Nernst equation below 500° C. Sensors equipped with electrodes of the present invention may therefore be used to measure the oxygen potential of gases (e.g. boiler flue gases, internal combustion engine exhausts) in the temperature range 300°–700° C., where sensors with conventional electrodes require supplementary heating to generate Nernstian emfs. For gases below 300° C., the electrodes of the present invention enable sensors to operate with supplementary heating to bring them to a temperature in the range 300°–400° C., whereas sensors with conventional electrodes are generally heated above 700° C. The lower operating temperature reduces the explosion hazard associated with maintaining a heated sensor in the flue of a combustion device such as a boiler.

The invention also includes an oxygen sensor which incorporates a solid electrode in accordance with the invention.

In the following description, reference will be made to the accompanying drawings, in which.

Figure 1:
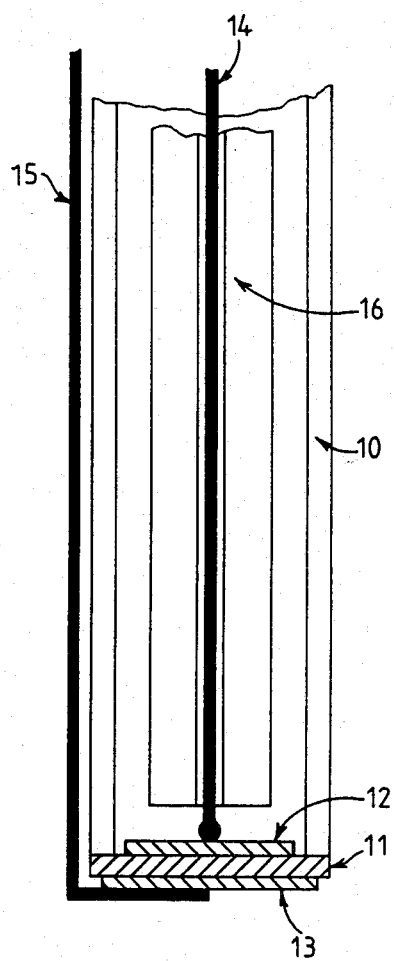
FIG. 1 shows a longitudinal section of an oxygen sensor embodying the electrodes of the invention.

One form of complete sensor for use in gases, incorporating the electrode materials of the present invention, is shown in FIG. 1. A hollow ceramic body 10 is closed at one end by a solid electrolyte disc 11. Electrodes 12 and 13 of a suitable urania-based solid solution are located at the inner and outer surfaces, respectively, of disc 11. Electrical contact to the electrodes is made by metal wires 14 and 15. Wire 14 is pressed against electrode 12 by spring loading (not shown), applied by means of insulating tube 16. Tube 16 may also be used to convey a reference gas, e.g., air, to electrode 12. If tube 16 is multi-bore, it may also carry a thermocouple to determine the temperature of electrolyte disc 11, in which case wire 14 may be one leg of the thermocouple.

An alternative to wires 14 and 15 for electrical contact to the electrodes 12 and 13 is to use coatings, e.g., of platinum, gold, palladium, silver or their alloys, or of the electrode material itself, particularly mixed with a nobel metal, on the inside and outside surfaces of ceramic body 10, extending from electrodes 12 and 13 to the open end of the sensor. Such coatings may completely cover the surfaces of ceramic body 10, or they may consist of continuous strips covering only part of ceramic body 10.

For use in molten metals, outer electrode 13 is not required. Electrical contact must be made to the molten metal in the vicinity of the sensor, using an electrical conductor such as wire 15 attached to the sensor but not in direct contact with solid electrolyte disc 11, or using a metallic coating on the outer surface of ceramic body 10 as hitherto described, or using a separate electrical conductor adjacent to the sensor. For measurements over extended periods, it is essential that the external electrical contact not dissolve in, or otherwise be attacked by, the molten metal. If a gaseous reference, e.g., air, is used the internal electrode 12 and electrical contact 14 are required.

A further alternative, for use in either gases or molten metals, is for the solid electrolyte to take the form of a closed-end tube or other similar hollow shape, replacing both disc 11 and ceramic body 10. Another alternative, particularly appropriate when measuring gases, is for the reference environment, e.g. air, to contact external electrode 13 and for the gas or molten metal under test to occupy the inside of the sensor. In the case of a gas, it may be conveyed to internal electrode 12 by means of tube 16.

The following examples illustrate the preparation and electrochemical properties of the electrodes of this invention, and the behaviour of solid electrolyte oxygen sensors incorporating such electrodes in the laboratory and in plant trials.

In the examples the subscript "$2\pm x$" used in the formulae indicates a small departure from an oxygen/metal atom ratio of 2. The magnitude and sign of the departure will depend on the uranium/dopant cation ratio and on the oxygen partial pressure and temperature to which the materials are exposed during processing. In general, x will be much less than 1, usually less than 0.1.

EXAMPLE 1

Two powders of composition $(U_{0.5}Sc_{0.5})O_{2\pm x}$ and $(U_{0.38}Sc_{0.62})O_{2\pm x}$ were prepared by coprecipitation of the hydroxides with ammonia from aqueous solutions containing the required proportions of uranyl nitrate and scandium nitrate, followed by drying and calcination in air. Room temperature x-ray diffraction after calcination showed that the fluorite solid solution structure was fully formed, with no residual traces of $Sc_2O_3$ or $U_3O_8$, after heating to 1060° C. for $(U_{0.5}Sc_{0.5})O_{2\pm x}$ and to 900° C. for $(U_{0.38}Sc_{0.62})O_{2\pm x}$. The structural stability of both materials was demonstrated by the observation that no change occurred in their room temperature x-ray diffraction patterns after the powders were heated in 90 volume percent $N_2$+10 volume percent $H_2$ at 900° C. for 22 hours. Both powders retained the fluorite structure despite variation in the ratio: oxygen atoms/total metal atoms from >2 (air calcination) to <2 ($N_2/H_2$ calcination).

EXAMPLE 2

Fine pastes of $(U_{0.5}Sc_{0.5})O_{2\pm x}$ and $(U_{0.38}Sc_{0.62})O_{2\pm x}$ in triethylene glycol were prepared by grinding each powder with a 25 percent solution of triethylene glycol in ethanol until the ethanol had evaporated, and repeating this procedure several times. A similar procedure was used to prepare pastes comprising a mixture in triethylene glycol of 25 weight percent $PtO_2$ and 75 weight percent $(U_{0.5}Sc_{0.5})O_{2\pm x}$ or $(U_{0.38}Sc_{0.62})O_{2\pm x}$.

These pastes were painted on both sides of yttria stabilized zirconia solid electrolyte discs with a paint brush, for electrochemical measurements. The discs were heated to 600° C. in air to burn off the triethylene glycol and to decompose the $PtO_2$ to platinum. Room temperature x-ray diffraction confirmed that the $PtO_2$ did decompose to platinum metal without reacting either with the (U, Sc)$O_{2\pm x}$ or with the yttria stabilized zirconia at temperatures between 600° and 900° C.

The resistance at the interface between each electrode and the solid electrolyte disc was determined using complex impedance dispersion analysis to distinguish between the electrode and electrolyte contributions. For comparison, similar measurements were carried out on yttria stabilized zirconia discs provided with porous platinum electrodes either by sputtering or by coating with platinum paste (Hanovia Liquid Gold No. 6082). Measurements were performed after heat treatment at 600° C., 750° C. and 900° C., the resistances being determined at temperatures extending from the heat treatment temperature down to 500° C.

After heating to 600° C., the electrode resistances followed the order:

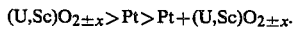

However, on heating to 750° C. and particularly to 900° C. the resistance of the $(U_{0.5}Sc_{0.5})O_{2\pm x}$ and $(U_{0.38}Sc_{0.62})O_{2\pm x}$ electrodes decreased markedly due to improved contact between the electrode and the electrolyte, whereas the resistance of the platinum electrodes increased greatly. With mixtures of Pt and (U, Sc)$O_{2\pm x}$ the electrode resistance varied with heat treatment temperature in a manner which was intermediate between that of platinum and the (U, Sc)$O_{2\pm x}$.

Figure 2:
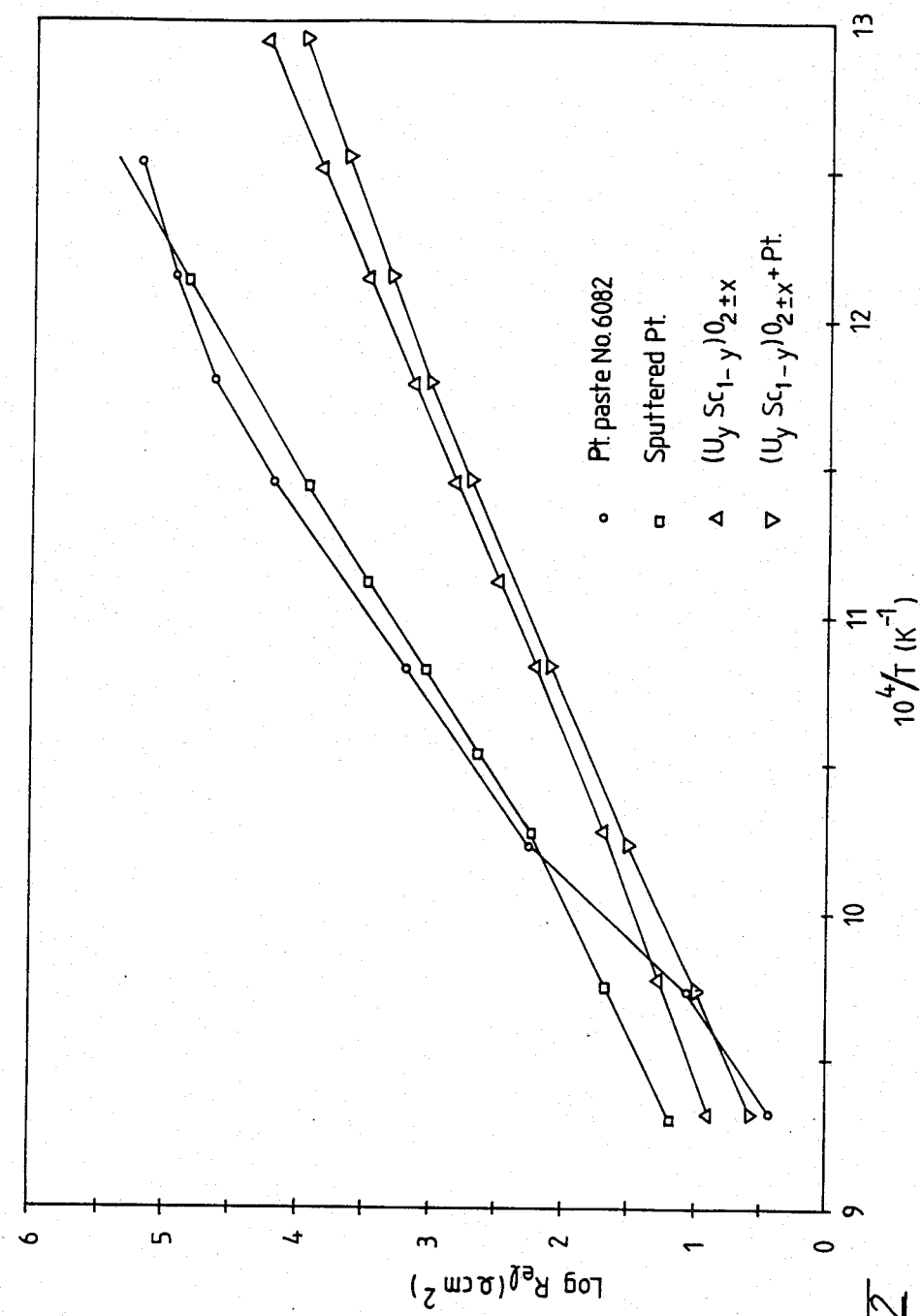
FIGS. 2 to 6 are graphs showing the performance of the electrodes and electrode materials of the invention, including comparative results for conventional metal electrodes.

After heat treatment at 900° C. there was little difference in the electrode resistance of (U, Sc)$O_{2\pm x}$ and Pt+(U, Sc)$O_{2\pm x}$, as shown in FIG. 2 in which the logarithm of electrode resistance $R_{el}$ is plotted against the reciprocal of absolute temperature for all four types of electrode. The resistance of the platinum electrodes was generally higher, particularly at low temperature where they were higher in resistance by a factor of ten. These results strongly suggest that, from the point of view of electrode resistance, electrodes based on (U, Sc)$O_{2\pm x}$ solid solutions, with or without a noble metal such as platinum, are superior to conventional porous metal electrodes at temperatures below 700° C.

EXAMPLE 3

Six sensors of the type shown in FIG. 1 were prepared, each one with a different pair of electrodes. In every case the electrolyte disc comprised a sintered mixture of 50 weight percent $Al_2O_3$ and 50 weight percent of a $ZrO_2$-$Sc_2O_3$ solid solution containing 4.7 mole percent $Sc_2O_3$. Three of the sensors were given electrodes of (U, Sc)$O_{2\pm x}$ plus $PtO_2$ as described in Example 2, the U/Sc ratio being 0.38/0.62 (one sensor, thin electrode coatings) or 0.5/0.5 (two sensors, one with thin coatings and the other with thick coatings). For comparison, the other three sensors were supplied with porous platinum electrodes, one by the in-situ decomposition of chloroplatinic acid, the second and third by painting with commercial platinum pastes (Hanovia Liquid Gold No. 6082 and No. 8907 respectively). All electrodes were fired in air at 600° C. prior to testing, resulting in the decomposition of the $PtO_2$ to platinum metal.

Sensor performance tests were carried out between 300° C. and 600° C. These tests comprised the determination of the cell voltage (E) with air at both electrodes and with air at the inner electrode and $O_2$-$N_2$ mixtures (1 to 100 percent $O_2$) at the outer electrode, and the effect on cell voltage of varying the internal air flow rate and, at 300° to 450° C., of interchanging the internal and external gases. Most tests were performed at intervals of 25° C., during both heating and cooling. All tests were repeated after the sensors had been reheated in air, first to 750° C. and then to 900° C.

Figure 3:
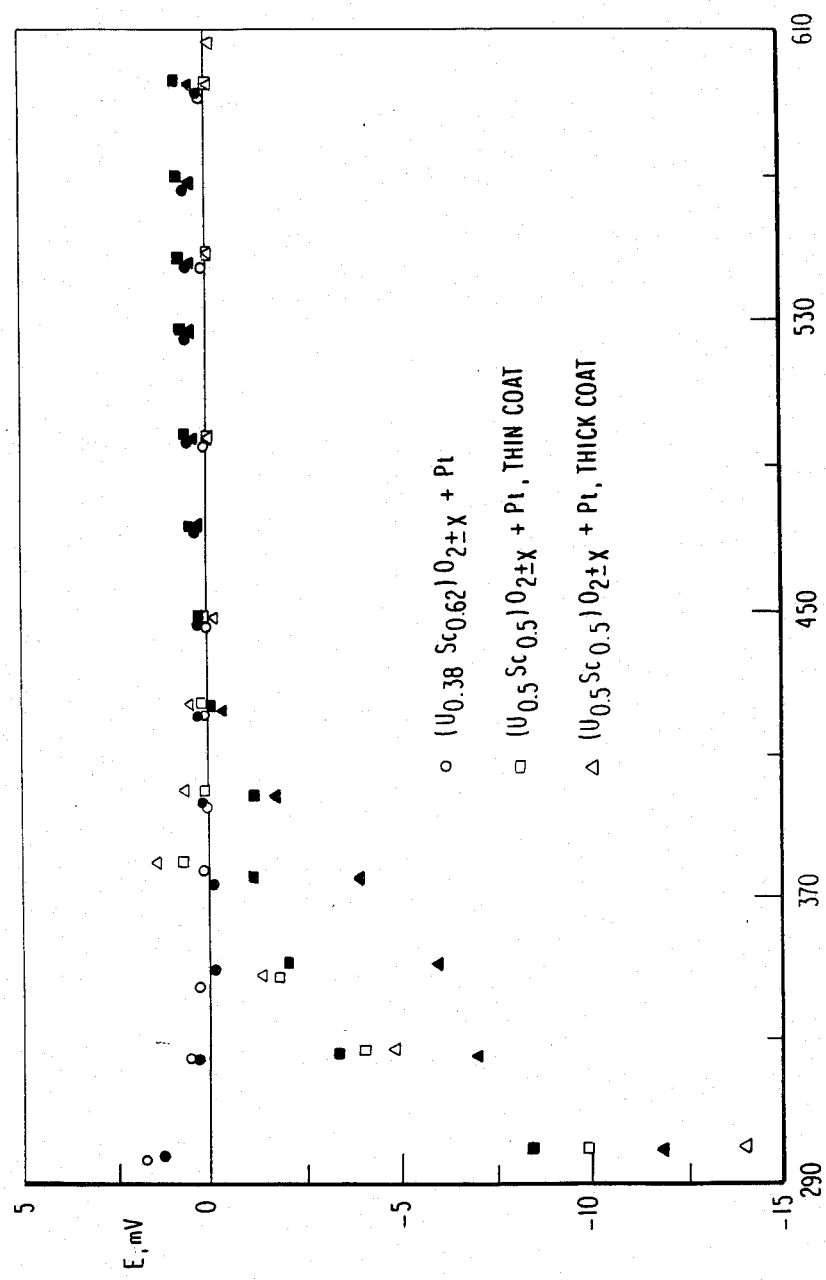
Figure 4:
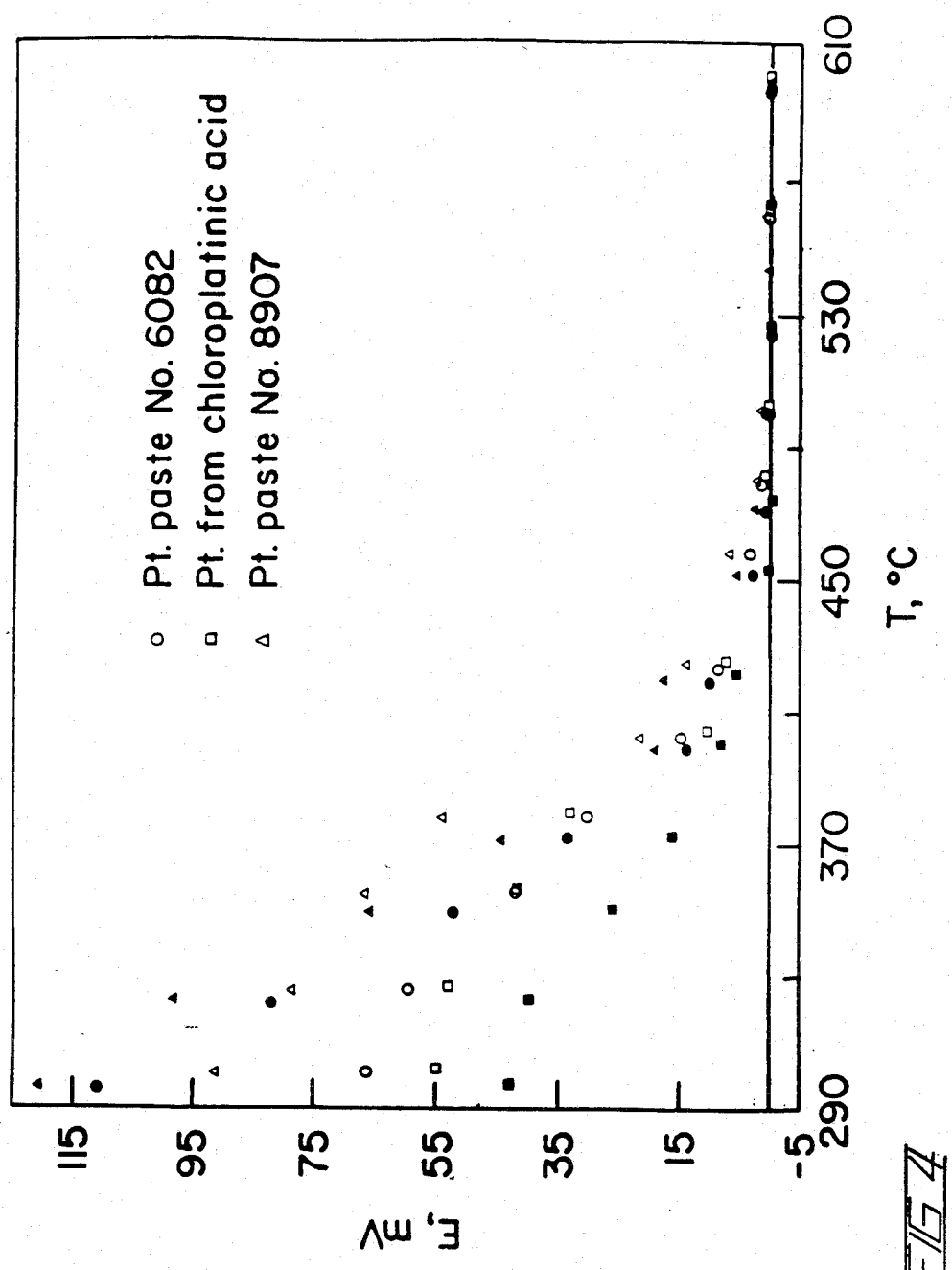

Results of the air/air tests after firing to 600° C. are shown in FIG. 3 [(U, Sc)$O_{2\pm x}$+Pt electrodes] and in FIG. 4 (porous Pt electrodes). The solid lines in these and the following two figures represent the theoretical voltage, zero in this case. The open symbols correspond to data obtained during heating, and the closed symbols are cooling data.

Figure 5:
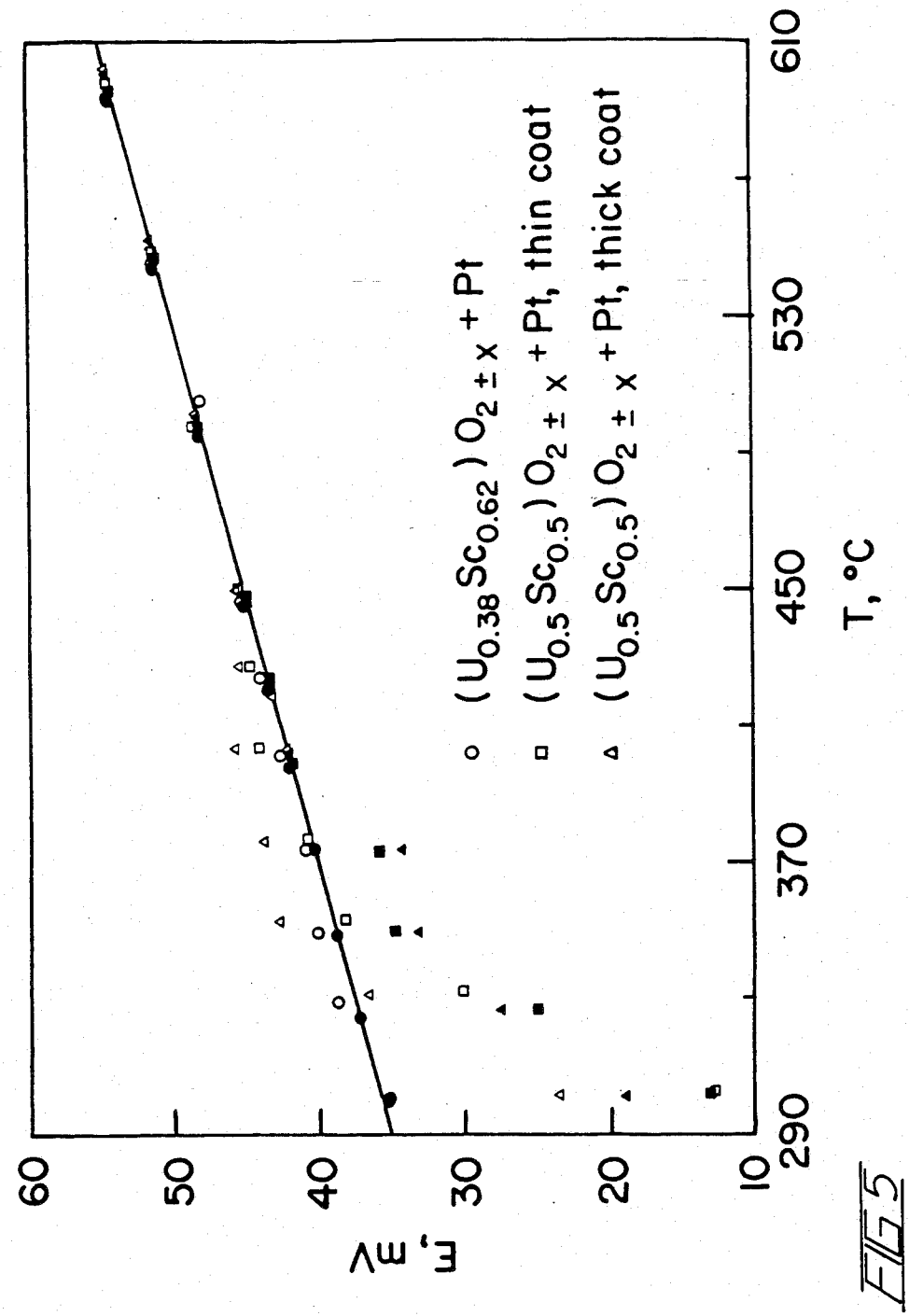
Figure 6:
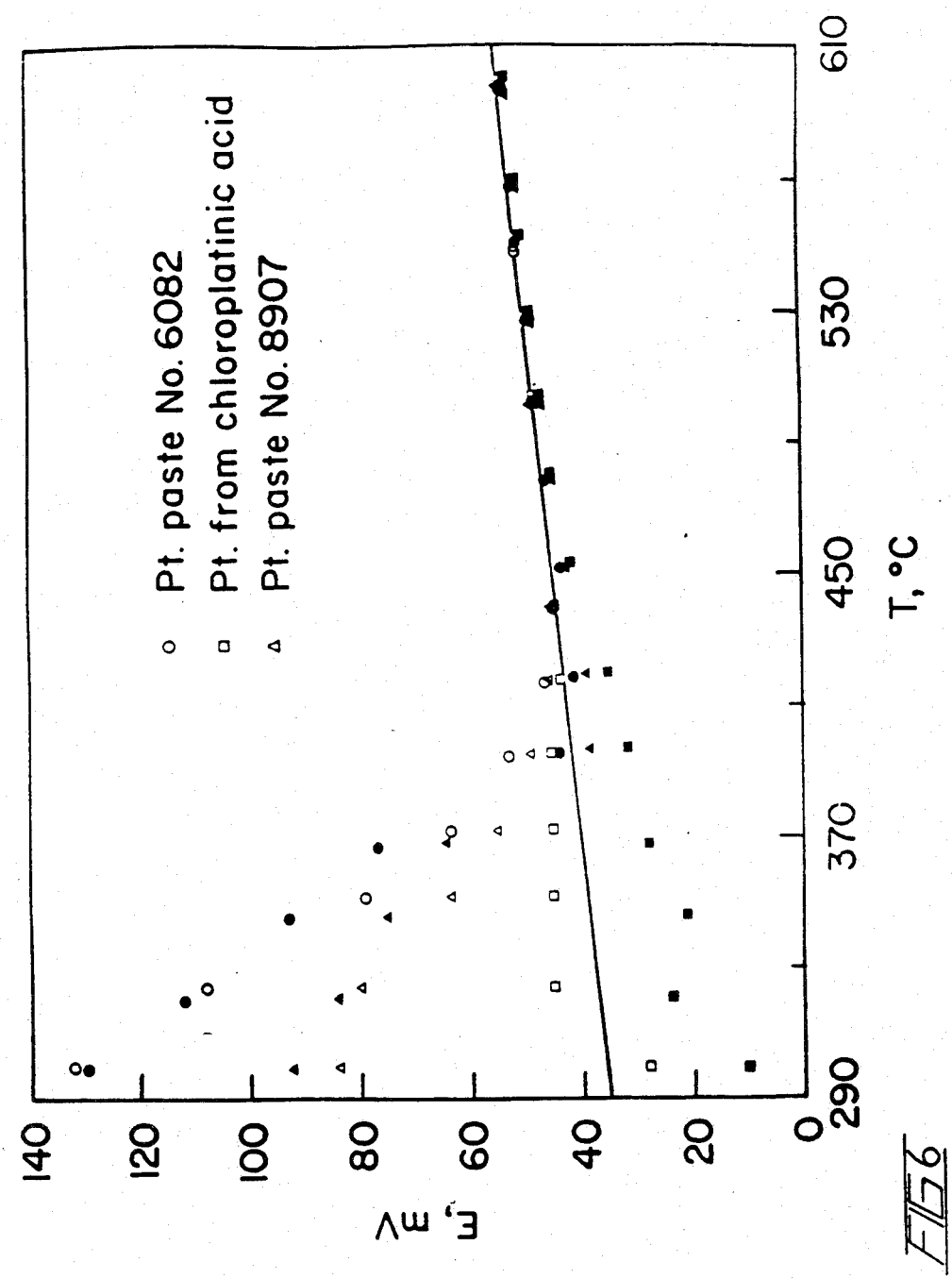

FIG. 4 shows that all sensors with platinum electrodes gave significant zero errors below about 450° C. In contrast, those with $(U_{0.5}Sc_{0.5})O_{2\pm x}$+Pt electrodes were satisfactory down to about 370° C., and the sensor with $(U_{0.38}Sc_{0.62})O_{2\pm x}$+Pt electrodes showed little error even at 300° C. Identical trends were evident in the air versus $O_2/N_2$ tests, for example those with 1.15 percent oxygen in nitrogen (FIGS. 5 and 6). A dependence of the cell voltage on air flow rate was evident only below these "breakdown temperatures", as was the failure to achieve ideal cell voltages after interchanging the internal and external gases. In general, the sensors with platinum electrodes exhibited higher resistances than those with the urania-scandia-platinum electrodes.

Heating to 750° C. and 900° C. caused no substantial deterioration in behaviour of the urania-scandia-platinum electrodes. On the other hand, the total resistance and the "breakdown temperature" of each sensor with platinum electrodes increased progressively with the pretreatment temperature.

These results demonstrate the superior low temperature performance of electrodes incorporating urania-scandia solid solutions over conventional porous platinum electrodes on solid electrolyte oxygen sensors. In particular, the electrode material consisting of platinum and $(U_{0.38}Sc_{0.62})O_{2\pm x}$ enables oxygen sensors to operate reliably at temperatures as low as 300° C., well below the limit of similar sensors fitted with porous platinum electrodes.

EXAMPLE 4

A powder of composition $(U_{0.4}Pr_{0.6})O_{2\pm x}$ was prepared by coprecipitation of the hydroxides with ammonia from an aqueous solution containing the required amounts of uranyl and praeseodymium nitrates, followed by drying. This powder was divided into four portions, and calcined in air for 24 hours using a different temperature for each portion to produce powders with different grain sizes and surface areas. The temperatures used were 600°, 700°, 800° and 900° C. X-ray diffraction after calcination confirmed that reaction was complete, each powder showing only a single fluorite phase.

Fine pastes of composition 25 weight percent $PtO_2$ and 75 weight percent $(U_{0.4}Pr_{0.6})O_{2\pm x}$ in triethylene glycol were prepared from each powder using the procedure described in Example 2. Sensors were prepared and tested as described in Example 3, using these pastes to form electrodes. All sensors gave Nernstian behaviour down to 300°–350° C. with air as the internal atmosphere and air, 5 percent $O_2$, 1 percent $O_2$ and 0.14 percent $O_2$ in $N_2$ as the external atmosphere. The lowest operating temperature was achieved using the $(U_{0.4}Pr_{0.6})O_{2\pm x}$ powder which had been calcined at the lowest temperature (600° C.).

EXAMPLE 5

Plant trials were performed in the exhaust duct of a natural gas-fired furnace used for calcining gypsum, where the exhaust gas temperature varied between 400° C. and 485° C. and the oxygen concentration between 3.9 and 6.8 percent. Sensors were mounted in a conventional high temperature oxygen probe assembly protruding horizontally into the duct. For comparison, a gas sampling line was fitted just above the probe and a small pump was used to extract a continuous gas sample which was fed, via a water trap, to a conventional oxygen analyser incorporating a zirconia sensor held at 800° C. Sensors in the in-situ probe were protected from gypsum dust by a filter pad of alumina fibre.

Three different low temperature sensors were tested. Each was of the type shown in FIG. 1 and described in Example 3, the difference being the electrode materials used. The first sensor contained electrodes comprising a mixture of platinum paste (Hanovia Liquid Gold No. 6082, 20 weight percent) and $(U_{0.6}Y_{0.4})O_{2\pm x}$ (80 weight percent), prepared and applied in a manner similar to the urania-scandia-platinum electrodes described in Examples 2 and 3. This sensor operated for six months, for the first five of these giving readings identical with those of the sampling analyser within a standard deviation of 0.5 percent oxygen. During the sixth month the test sensor gave oxygen readings which were 2 percent or more high. On removal the sensor was found to have developed gas leaks sufficient to explain this error, probably due to thermal cycling immediately prior to malfunctioning.

The second sensor contained electrodes of platinum only, formed by decomposing chloroplatinic acid to give a thin coat of platinum metal over which was applied platinum paste (Hanovia Liquid Gold No. 6082). To avoid degrading the electrochemical activity of these electrodes, they were fired at only 550° C. The sensor was tested in the duct for one month, during which time it consistently gave oxygen concentration readings 2 to 3 percent lower than those indicated by the sampling analyser. On removal and inspection, no evidence was found of contamination by gypsum dust. The errors are attributed to non-ideal behaviour of the type illustrated for platinum electrodes in FIGS. 4 and 6.

The final sensor had electrodes of $PtO_2$ (25 weight percent) and $(U_{0.38}Sc_{0.62})O_{2\pm x}$ (75 weight percent), prepared and applied as described in Examples 2 and 3. It was tested in the duct for three weeks, agreeing with the sampling analyser within a standard deviation of 0.25 percent oxygen. The probe assembly was then removed.

These plant trials showed that sensors equipped with urania-based electrodes of the present invention could be used to monitor oxygen in combustion product gases at temperatures of 400° C. to 480° C. The tests also showed that similar sensors equipped with platinum metal electrodes failed to give accurate readings under similar conditions.

EXAMPLE 6

A sensor of the type shown in FIG. 1 and described in Example 3, supplied with electrodes of $PtO_2$ (25 weight percent) and $(U_{0.38}Sc_{0.62})O_{2\pm x}$ (75 weight percent), was fitted in an oxygen probe assembly and mounted in the exhaust chimney of a small oil-fired boiler. At this spot, the gas temperature varied from 200° C. (burner off) to 240° C. (burner on). A small electrical heater around the tip of the sensor maintained the solid electrolyte disc and electrodes at 350°–400° C. Over a period of six months the probe readings taken during boiler operation were compared against measurements made with a sampling system and separate analyser as described in Example 5. Provided that the sensor tip in the test probe was surrounded with a platinum-loaded catalytic filter to oxidise any unburnt combustibles, satisfactory agreement was obtained for typical values between 8 and 10 percent oxygen.

We claim:

1. An oxygen sensor comprising an oxygen ion-conducting solid electrolyte member and at least one electrode comprising a surface layer on the solid electrolyte, wherein said surface layer contains: (1) at least one noble metal selected from the group consisting of platinum, gold, palladium, silver and alloys of any two or more of these elements, and (2) a solid solution in uranium oxide of one or more other metal oxides with an oxygen/metal atom ratio equal to or less than two, provided that at least one of said other metal oxides has an oxygen/metal atom ratio less than two.

2. An oxygen sensor as claimed in claim 1 wherein the surface layer consists of a porous coating of particles containing said solid solution in uranium oxide.

3. An oxygen sensor as claimed in claim 2 wherein in addition to the solid solution in uranium oxide, the porous coating contains a proportion of free uranium oxide and/or of the other oxide component or components of the solid solution.

4. An oxygen sensor as claimed in claim 2 wherein the said other oxide has an oxygen/metal atom ratio less than two and the solid solution in uranium oxide has a face-centered cubic crystal structure.

5. An oxygen sensor as claimed in claim 4 wherein the said other oxide is selected from the group consisting of $Sc_2O_3$, $Dy_2O_3$, $Y_2O_3$, and $PrO_y$, where $y<2$.

* * * * *